(12) United States Patent
Rahaman et al.

(10) Patent No.: US 11,963,907 B2
(45) Date of Patent: Apr. 23, 2024

(54) MULTI-USE BEAM SAMPLER IN LASER BEAM DELIVERY PATH OF OPHTHALMIC LASER SYSTEM

(71) Applicant: AMO Development, LLC, Santa Ana, CA (US)

(72) Inventors: Mohammad Saidur Rahaman, Santa Clara, CA (US); Hong Fu, Pleasanton, CA (US)

(73) Assignee: AMO Development, LLC, Irvine, CA (US)

(*) Notice: Subject to any disclaimer, the term of this patent is extended or adjusted under 35 U.S.C. 154(b) by 392 days.

(21) Appl. No.: 17/448,175

(22) Filed: Sep. 20, 2021

(65) Prior Publication Data

US 2022/0087862 A1    Mar. 24, 2022

Related U.S. Application Data

(60) Provisional application No. 63/081,081, filed on Sep. 21, 2020.

(51) Int. Cl.
*A61F 9/008*     (2006.01)
*G01J 1/42*      (2006.01)
(Continued)

(52) U.S. Cl.
CPC .......... *A61F 9/008* (2013.01); *G01J 1/4257* (2013.01); *G02B 26/0875* (2013.01); *G02B 27/108* (2013.01); *A61B 2018/20553* (2017.05)

(58) Field of Classification Search
CPC .... A61F 9/008; A61F 9/00814; A61F 9/0084; G01J 1/4257; G02B 26/0875; G02B 27/108; A61B 2018/20553
See application file for complete search history.

(56) References Cited

U.S. PATENT DOCUMENTS

| 4,492,436 A | 1/1985 | Bergmann |
| 5,095,476 A | 3/1992 | Greve et al. |

(Continued)

FOREIGN PATENT DOCUMENTS

| JP | S63119024 A | 5/1988 |
| WO | 2011091326 A1 | 7/2011 |

(Continued)

OTHER PUBLICATIONS

Beamsplitter Guide. https://www.thorlabs.com/newgrouppage9.cfm?objectgroup_id=9028 (Year: 2023).*

*Primary Examiner* — Hwa Andrew Lee
(74) *Attorney, Agent, or Firm* — Johnson & Johnson Surgical Vision, Inc.

(57) ABSTRACT

In a laser beam delivery system for an ophthalmic laser system, a single multi-use beam sampler is employed to form three sampled laser beams, including two for redundant laser energy monitoring and one for laser focal point depth measurement. The beam sampler is a transparent plate with preferably parallel front and back surfaces. The front surface reflects a fraction of the incoming beam to form the first sampled beam toward an energy monitoring detector. The back surface reflects another fraction of the beam to form a second sampled beam exiting backwardly from the front surface toward another energy monitoring detector. An objective lens focuses the transmitted beam onto a target, and collects back reflected or scattered light from the target to form a return beam. The back surface of the beam sampler reflects a fraction of the return beam to form the third sampled beam toward a third detector.

20 Claims, 2 Drawing Sheets

(51) Int. Cl.
    *G02B 26/08*    (2006.01)
    *G02B 27/10*    (2006.01)
    *A61B 18/20*    (2006.01)

(56)            References Cited

U.S. PATENT DOCUMENTS

| | | |
|---|---|---|
| 5,185,731 A | 2/1993 | Takahashi |
| 5,309,422 A | 5/1994 | Kuroki et al. |
| 5,337,299 A | 8/1994 | Takahashi |
| 5,726,962 A | 3/1998 | Okada et al. |
| 5,771,122 A | 6/1998 | Shuman |
| 5,777,975 A | 7/1998 | Horinouchi et al. |
| 5,808,739 A | 9/1998 | Turner et al. |
| 6,074,384 A | 6/2000 | Brinkmann et al. |
| 6,128,133 A | 10/2000 | Bergmann |
| 6,608,674 B2 | 8/2003 | Gerlach et al. |
| 7,283,251 B1 | 10/2007 | Tansey |
| 7,420,686 B2* | 9/2008 | Tan .................. G01J 3/36 356/454 |
| 2004/0070831 A1 | 4/2004 | Nishimura |
| 2007/0236793 A1* | 10/2007 | Stark |
| 2018/0221200 A1* | 8/2018 | Witowski ............... A61F 9/0084 |
| 2020/0064622 A1* | 2/2020 | Rahaman ........... G02B 26/0875 |

FOREIGN PATENT DOCUMENTS

| | | | |
|---|---|---|---|
| WO | 2015119892 A1 | 8/2015 | |
| WO | 2017196306 A1 | 11/2017 | |

* cited by examiner

MULTI-USE BEAM SAMPLER IN LASER BEAM DELIVERY PATH OF OPHTHALMIC LASER SYSTEM

CROSS-REFERENCE TO RELATED APPLICATIONS

This application claims the benefit under 35 U.S.C. § 119(e) of U.S. Provisional Patent Application No. 63/081,081, filed Sep. 21, 2020, which is incorporated herein by reference in its entirety.

BACKGROUND OF THE INVENTION

Field of the Invention

This invention relates to ophthalmic laser surgical systems, and in particular, it relates to a laser beam delivery system for an ophthalmic laser surgical system.

Description of Related Art

In ophthalmic laser surgical systems, to meet relevant safety requirements, the energy monitoring component must function in a redundant way to monitor the laser power delivered to the surgical target. In a typical ophthalmic laser surgical system, small fractions of the laser beams are picked at two places and sent towards two independent detectors to monitor the laser energy or power.

In some ophthalmic laser surgical systems, a beam splitter is used to direct a small fraction of the return laser beam to a light intensity detector for the purpose of calibrating and measuring the depth position of the laser focal point. The return laser beam refers to the laser beam that has been focused on the target (e.g. the eye or other target) by the objective lens, backward reflected or scattered by the target, and collected by the objective lens to travel backwards along the laser beam path. One such laser system is described in commonly owned U.S. Pat. Appl. Pub. No. 2020/0064622, entitled "Detection of Optical Surface of Patient Interface for Ophthalmic Laser Applications Using a Non-Confocal Configuration."

SUMMARY

In an ophthalmic laser system which require three sampled beams to be formed (two for the separate laser energy monitoring detectors and one for the depth measurement detector), to use three separate beam samplers in the main laser beam path would result in significant optical losses and wavefront distortion.

Accordingly, the present invention is directed to a laser beam delivery system for an ophthalmic laser system that employs a single multi-use beam sampler to form three sampled beams. Such a system substantially obviates one or more of the problems due to limitations and disadvantages of the related art.

An object of the present invention is to provide a laser beam delivery system that has a simpler structure, reduced alignment complexity, and reduced optical losses and wavefront distortion.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve the above objects, the present invention provides an ophthalmic laser system which includes: a beam sampler, comprising a plate made of a transparent material with a front surface and a back surface, wherein the beam sampler is configured to receive a laser beam at the front surface, to form a first sampled beam by reflecting a first fraction of the laser beam by the front surface, to form a second sampled beam by reflecting a second fraction of the laser beam by the back surface, the second sampled beam exiting the front surface, and to transmit a portion of the laser beam out of the back surface; a first light detector and a second light detector respectively disposed to receive and detect the first sampled beam and the second sampled beam, the first and second light detectors being independent of each other; an objective lens, disposed to receive the laser beam transmitted through the beam sampler and to focus the laser beam to a focal point in a target, wherein the objective lens is further configured to receive a laser light reflected or scattered from the target to form a return beam toward the back surface of the beam sampler, wherein the beam sampler is further configured to form a third sampled beam by reflecting a fraction of the return beam by the back surface; and a third light detector disposed to receive the third sampled beam.

In another aspect, the present invention provides a method implemented in an ophthalmic laser system, the method including: by a beam sampler, the beam sampler being a plate made of a transparent material with a front surface and a back surface, receiving a laser beam at the front surface; by the beam sampler, reflecting a first fraction of the laser beam by the front surface to form a first sampled beam; by the beam sampler, reflecting a second fraction of the laser beam by the back surface to form a second sampled beam which exits the front surface; by the beam sampler, transmitting a portion of the laser beam out of the back surface; by a first light detector, receiving the first sampled beam; by a second light detector which is independent of the first light detector, receiving the second sampled beam; by an objective lens, receiving the laser beam transmitted through the beam sampler and to focusing the laser beam to a focal point in a target; by the objective lens, receiving a laser light reflected or scattered from the target to form a return beam toward the back surface of the beam sampler; by the beam sampler, reflecting a fraction of the return beam by the back surface to form a third sampled beam; and by a third light detector, receiving and detecting the third sampled beam.

In some embodiments, the beam sampler is a glass plate with un-coated parallel front and back surfaces.

It is to be understood that both the foregoing general description and the following detailed description are exemplary and explanatory and are intended to provide further explanation of the invention as claimed.

DETAILED DESCRIPTION OF PREFERRED EMBODIMENTS

Figure 2:
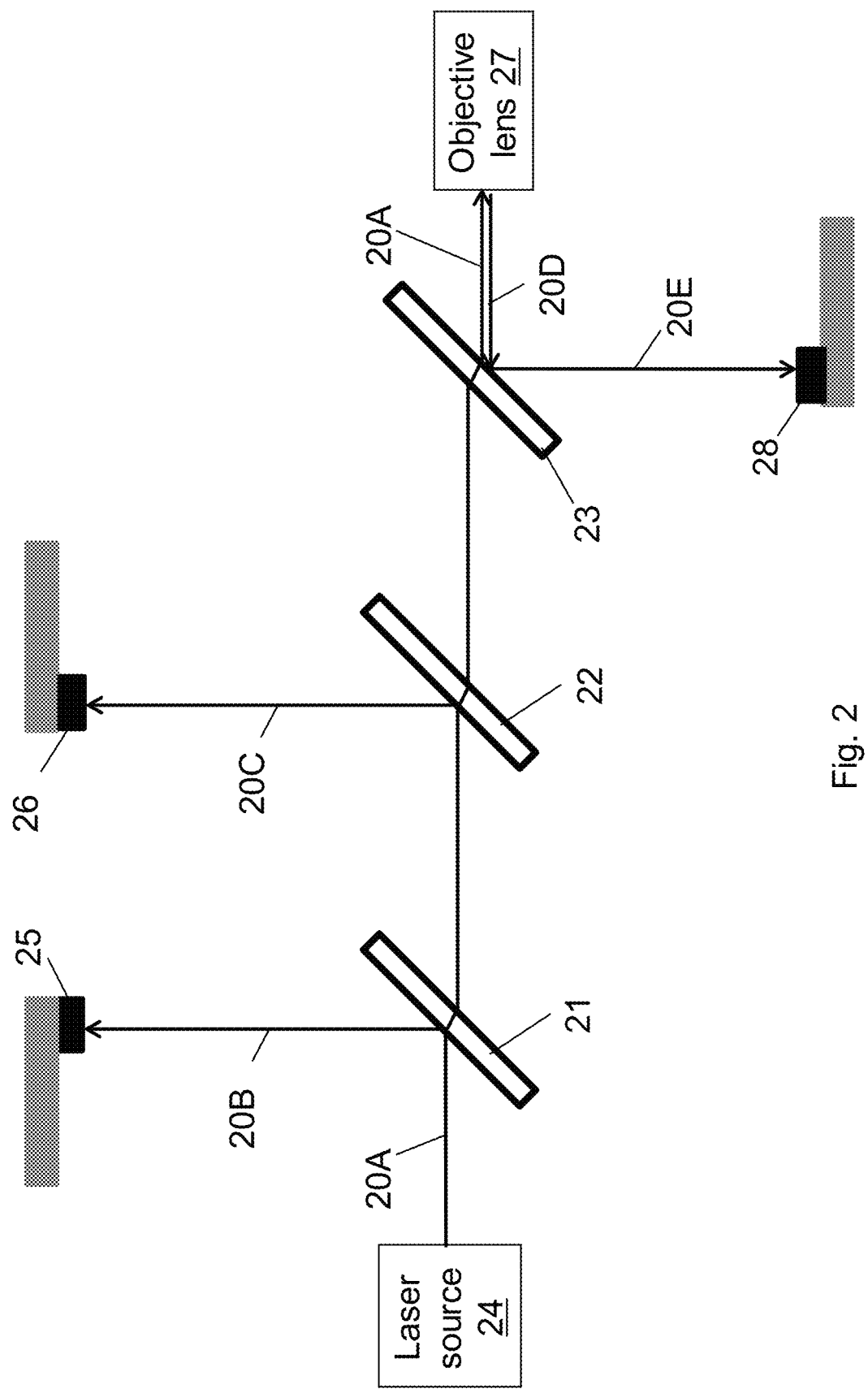
FIG. 2 schematically illustrates another laser beam delivery system for an ophthalmic laser surgical system which employs multiple separate beam samplers.

FIG. 2 schematically illustrates a laser beam delivery system for an ophthalmic laser surgical system which employs three separate beam samplers 21, 22 and 23. As shown in FIG. 2, the laser beam 20A generated by a laser source 24 sequentially passes through the first, second and third beam samplers 21, 22 and 23. Fractions 20B and 20C of the beam are reflected at the front surfaces of the first and second beam samplers 21 and 22, respectively, toward two independent energy monitoring detectors (i.e. photodiodes) 25 and 26, respectively. Detectors 25 and 26 provide redundant energy monitoring functions. After passing through the third beam sampler 23 (the reflection from this beam sampler is not shown), the laser beam 20A is focused by an objective lens 27 to the target (e.g. the eye, or a patient interface device, or other target, not shown in FIG. 2). The laser beam reflected and/or scattered from the target is collected by the objective lens as the return beam 20D, a fraction 20E of which is reflected at the back surface of the third beam sampler 23 toward a light intensity detector (i.e. photodiode) 28 for focal point depth measurement functions. The transmitted portion of the return beam is not shown in the drawing. Other optical components of the laser beam delivery system, such as shutters, mirrors, scanners, etc., are not shown in the drawing.

The beam samplers are transparent plates. In this optical system, there are six optical surfaces—the front and back surfaces of each beam sampler—that contribute to optical loses and wavefront distortion. Moreover, this configuration has significant optical system alignment complexity and related cost.

Figure 1:
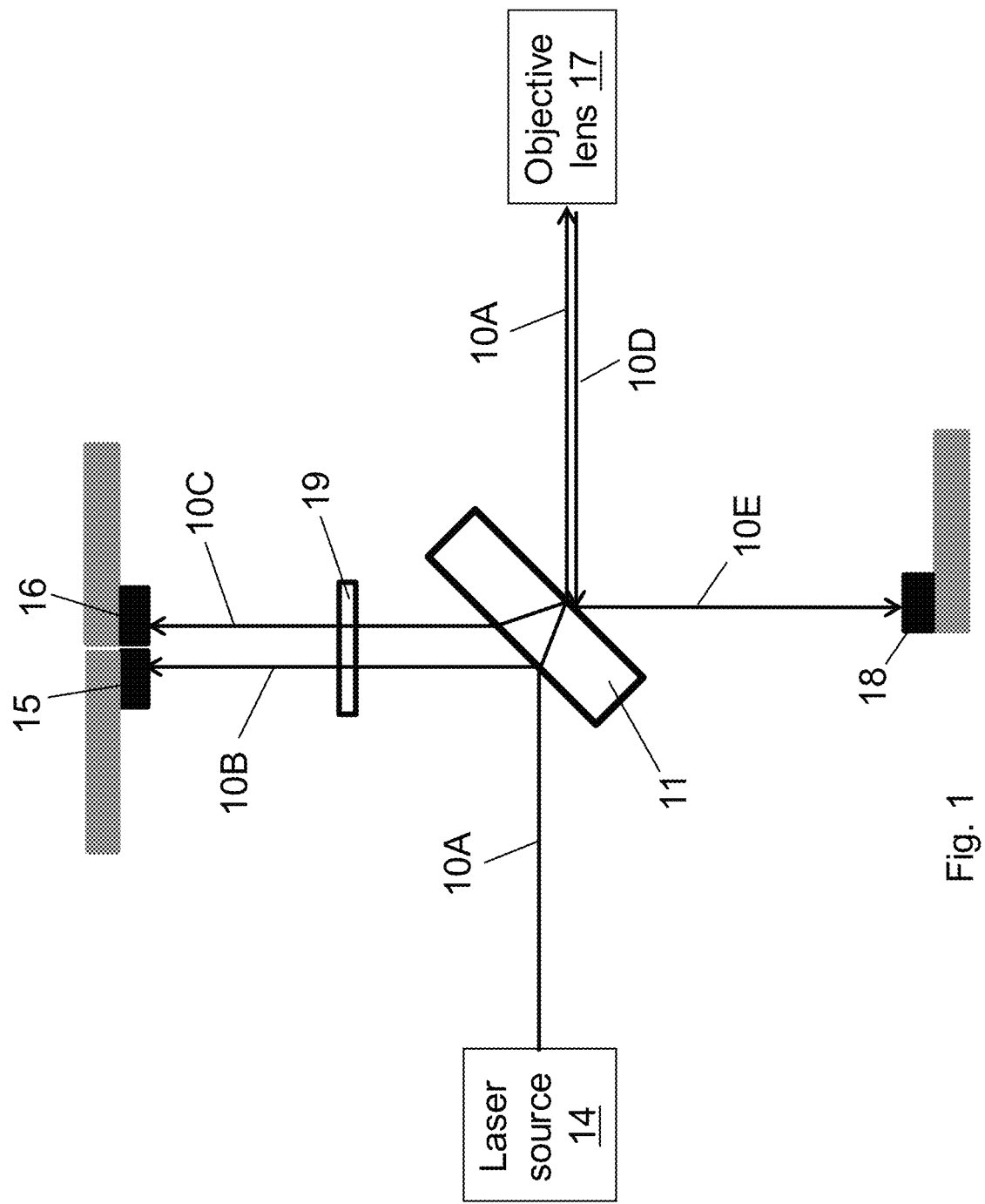
FIG. 1 schematically illustrates a laser beam delivery system for an ophthalmic laser surgical system which employs a single multi-use beam sampler according to an embodiment of the present invention.

FIG. 1 schematically illustrates a laser beam delivery system for an ophthalmic laser surgical system according to an embodiment of the present invention. This system employs a single beam sampler optical element 11, preferably a transparent plate with two optical surfaces, to form three sampled beams.

As shown in FIG. 1, when the laser beam 10A generated by a laser source 14 enters the beam sampler 11, a fraction of the beam is reflected at the front surface of the beam sampler, as a first sampled beam 10B, toward a first energy monitoring detector (i.e. photodiode) 15. After traveling through the interior of the beam sampler, another fraction of the beam is reflected at the back surface of the beam sampler, travels back through the interior of the beam sampler, and exits the front surface as a second sampled beam 10C, toward a second energy monitoring detector (i.e. photodiode) 16. Detectors 15 and 16 are independent of each other and provide redundant energy monitoring functions.

After exiting the back surface of the beam sampler (and passing through any other optical components not shown in FIG. 1), the laser beam 10A is focused by an objective lens 17 to the target (e.g. the eye, or a patient interface device, or other target, not shown in the drawing). The laser beam reflected and/or scattered from the target is collected by the objective lens 17 as the return beam 10D. A fraction of the return beam is reflected at the back surface of the beam sampler 11, as a third sampled beam 10E, toward a light intensity detector (i.e. photodiode) 18 for focal point depth measurement functions. The transmitted portion of the return beam is not shown in the drawing. Note here that the return beam 10D is schematically shown in an offset manner with respect to the incoming beam 10A for ease of illustration, but the two beams actually overlap each other. The principle of focal point depth measurement using the sampled return beam is described in the above-mentioned U.S. Pat. Appl. Pub. No. 2020/0064622.

In preferred embodiments, the beam sampler is a glass plate with parallel front and back surfaces, with no coating on either surface. The reflectivity of an un-coated air-glass interface is a function of the refractive index of the glass, which is very stable over time. Such a surface typically has a weak reflectivity, for example, a few percent, which is also dependent on the incident angle and polarization of the incident light. In some preferred embodiments, the beam sampler is disposed at close to Brewster's angle (e.g., within ±12 degrees of Brewster's angle) with respect to the incoming laser beam 10A, and the incoming laser beam is p-polarized, so that the intensity of both the first sampled beam 10B and the second sampled beam 10C are very low, for example, both are only about 0.6% of that of the incoming laser beam (or more generally, between 0.4% and 0.8%).

For the return beam, in some preferred embodiments, the optical components between the beam sampler 11 and the objective lens 17 are such that they do not substantially change the polarization of the laser light. In such a system, the return beam that has been reflected by the target will have approximately the same polarization as the incoming laser beam, so the reflectivity for the return beam at the back surface is also about 0.6%. In alternative embodiments, the return beam may have different polarization as the incoming laser beam, so the reflectivity for the return beam at the back surface may be different. When the laser light is scattered (as opposed to reflected) by the target, e.g. when cutting an eye tissue with the laser beam, the return beam will have a different polarization than the incoming laser beam. In such situations, the reflectivity of the return beam at the back surface of the beam sampler will be higher, for example, about 6-8%. This higher reflectivity is desirable for detecting weak back-scattered light.

In some alternative embodiments, the beam sampler may be a glass plate with coated surfaces, including antireflection coating, dichroic coating, metal coating, or other types of suitable coatings.

In preferred embodiments, the beam sampler 11 has parallel front and back surfaces and a sufficient thickness so that the first and second sampled beams 10B, 10C are spatially separate sufficiently to allow them to be incident on the two separate detectors 15 and 16. In one example, the thickness of the beam sampler 11 is 10 mm. When the refractive index of the glass plate is 1.45 and the incident angle is 45 degrees, this thickness gives a lateral deviation between the incoming laser beam and the transmitted laser beam of 3.15 mm, and a distance between the parallel first and second sampled beams 10B and 10C of 7.6 mm. The first and second energy monitoring detectors 15 and 16 are properly sized and positioned to separately receive the first and second sampled beams, respectively. More generally, the beam sampler 11 may be 10 mm to 20 mm thick.

In some alternative embodiments, the beam sampler may be a plate with two non-parallel surfaces. In such an embodiment, the first and second sampled beams will be non-parallel to each other, and the positions of the first and second energy monitoring detectors 15 and 16 and the depth measurement detector 18 should be adjusted accordingly.

One or more filters 19 (i.e., color filters, polarization filters, etc.) may be provided on the paths of the first and second sampled beams 10B and 10C. Other optical components of the laser beam delivery system, such as shutters, mirrors, scanners, etc., are not shown in the drawing. These components may be located between the laser source 14 and the beam sampler 11 and/or between the beam sampler and the objective lens 17.

To summarize, embodiments of the present invention employ a single beam sampler with two optical surfaces in the laser beam delivery path of an ophthalmic laser system to form three sampled beams, two for redundant laser energy monitoring and one for focal point depth measurement. Only two optical surfaces are present on the optical path to achieve the beam sampling functions, as compared to using three separate beam samplers with six optical surfaces in the system shown in FIG. 2. The optical loss and wavefront distortion is reduced three-fold. Moreover, the system is more robust as the laser alignment complexity is also reduced three-fold. This design also reduces cost.

It will be apparent to those skilled in the art that various modification and variations can be made in the ophthalmic laser beam delivery system of the present invention without departing from the spirit or scope of the invention. Thus, it is intended that the present invention cover modifications and variations that come within the scope of the appended claims and their equivalents.

What is claimed is:

1. An ophthalmic laser system comprising:
   a beam sampler, comprising a plate made of a transparent material with a front surface and a back surface, wherein the beam sampler is configured to receive a laser beam at the front surface, to form a first sampled beam by reflecting a first fraction of the laser beam by the front surface, to form a second sampled beam by reflecting a second fraction of the laser beam by the back surface, the second sampled beam exiting the front surface, and to transmit a portion of the laser beam out of the back surface;
   a first light detector and a second light detector respectively disposed to receive and detect the first sampled beam and the second sampled beam, the first and second light detectors being independent of each other;
   an objective lens, disposed to receive the laser beam transmitted through the beam sampler and to focus the laser beam to a focal point in a target, wherein the objective lens is further configured to receive a laser light reflected or scattered from the target to form a return beam toward the back surface of the beam sampler,
   wherein the beam sampler is further configured to form a third sampled beam by reflecting a fraction of the return beam by the back surface; and
   a third light detector disposed to receive the third sampled beam.

2. The ophthalmic laser system of claim 1, wherein the beam sampler is a transparent plate.

3. The ophthalmic laser system of claim 1, wherein the beam sampler is a glass plate with un-coated front and back surfaces.

4. The ophthalmic laser system of claim 3, wherein the front and back surfaces of the beam sampler are parallel to each other.

5. The ophthalmic laser system of claim 4, wherein the beam sampler is disposed within ±12 degrees of a Brewster's angle relative to the received laser beam.

6. The ophthalmic laser system of claim 1, wherein the front and back surfaces of the beam sampler are parallel to each other and the beam sampler has a thickness of 10 to 20 mm.

7. The ophthalmic laser system of claim 1, wherein the beam sampler is a glass plate with coated front and back surfaces.

8. The ophthalmic laser system of claim 1, wherein the first, second and third light detectors are photodiodes.

9. The ophthalmic laser system of claim 1, further comprising one or more filters disposed between the front surface of the beam sampler and the first and second light detectors.

10. The ophthalmic laser system of claim 1, further comprising a laser source configured to generate the laser beam.

11. A method implemented in an ophthalmic laser system, the method comprising:
    by a beam sampler, the beam sampler being a plate made of a transparent material with a front surface and a back surface, receiving a laser beam at the front surface;
    by the beam sampler, reflecting a first fraction of the laser beam by the front surface to form a first sampled beam;
    by the beam sampler, reflecting a second fraction of the laser beam by the back surface to form a second sampled beam which exits the front surface;
    by the beam sampler, transmitting a portion of the laser beam out of the back surface;
    by a first light detector, receiving the first sampled beam;
    by a second light detector which is independent of the first light detector, receiving the second sampled beam;
    by an objective lens, receiving the laser beam transmitted through the beam sampler and to focusing the laser beam to a focal point in a target;
    by the objective lens, receiving a laser light reflected or scattered from the target to form a return beam toward the back surface of the beam sampler;
    by the beam sampler, reflecting a fraction of the return beam by the back surface to form a third sampled beam; and
    by a third light detector, receiving and detecting the third sampled beam.

12. The method of claim 11, wherein the beam sampler is a transparent plate.

13. The method of claim 11, wherein the beam sampler is a glass plate with un-coated front and back surfaces.

14. The method of claim 13, wherein the front and back surfaces of the beam sampler are parallel to each other.

15. The method of claim 14, wherein the beam sampler is disposed within ±12 degrees of a Brewster's angle relative to the received laser beam.

16. The method of claim 11, wherein the front and back surfaces of the beam sampler are parallel to each other and the beam sampler has a thickness of 10 to 20 mm.

17. The method of claim 11, wherein the beam sampler is a glass plate with coated front and back surfaces.

18. The method of claim 11, wherein the first, second and third light detectors are photodiodes.

19. The method of claim 11, further comprising:
    by one or more filters, filtering the first and second sampled beams.

20. The method of claim 11, further comprising:
    by a laser source, generating the laser beam.

* * * * *